United States Patent [19]

Ammann et al.

[11] Patent Number: 5,409,896
[45] Date of Patent: Apr. 25, 1995

[54] TGF-β COMPOSITION FOR INDUCING BONE GROWTH

[75] Inventors: Arthur J. Ammann, San Rafael; Christopher G. Rudman, San Francisco, both of Calif.

[73] Assignee: Genentech, Inc., South San Francisco, Calif.

[21] Appl. No.: 132,405

[22] Filed: Nov. 12, 1993

Related U.S. Application Data

[60] Continuation of Ser. No. 63,841, May 18, 1993, which is a continuation of Ser. No. 790,856, Nov. 12, 1991, abandoned, which is a division of Ser. No. 401,906, Sep. 1, 1989, Pat. No. 5,158,934.

[51] Int. Cl.$^6$ .................. C12N 15/00; C07K 13/00; A61K 37/02
[52] U.S. Cl. ........................................ 514/13; 514/21
[58] Field of Search ................... 514/12, 21, 900

[56] References Cited

U.S. PATENT DOCUMENTS

| | | | |
|---|---|---|---|
| 4,563,350 | 1/1986 | Nathan et al. | 424/549 |
| 4,642,120 | 2/1987 | Nevo et al. | 623/16 |
| 4,702,734 | 10/1987 | Terranova et al. | 604/54 |
| 4,717,939 | 1/1988 | Baker | 424/549 |
| 4,768,570 | 9/1988 | Kuberasampath | 514/21 |
| 4,774,228 | 9/1988 | Seyedin et al. | 514/21 |
| 4,774,322 | 9/1988 | Seyedin | 530/350 |
| 4,810,691 | 3/1989 | Seyedin et al. | 514/21 |
| 4,843,063 | 6/1989 | Seyedin et al. | 514/21 |
| 4,863,732 | 9/1989 | Nathan et al. | 424/549 |
| 4,919,939 | 4/1990 | Baker | 424/493 |
| 4,968,590 | 11/1990 | Kuberasampath | 424/549 |
| 5,158,934 | 10/1992 | Amann | 514/21 |

FOREIGN PATENT DOCUMENTS

| | | |
|---|---|---|
| 0169016 | 1/1986 | European Pat. Off. . |
| 0182483 | 5/1986 | European Pat. Off. . |
| 0200341 | 12/1986 | European Pat. Off. . |
| 0267463 | 5/1988 | European Pat. Off. . |
| 0268561 | 5/1988 | European Pat. Off. . |
| 0268561 | 5/1988 | European Pat. Off. . |

OTHER PUBLICATIONS

Cheifetz et al., "The Transforming Growth Factor-β Systems, a Complex Pattern of Cross-Reactive Ligands and Receptors", *Cell*, 48:409-415 (1987).

Dernyck et al., "A new type of transforming growth factor-β, TGF-β3", *EMBO Jour.*, 7(12):3737-3743 (1988).

Derynck et al., "The Murine Transforming Growth Factor-β Precursor", *J. Biol. Chem.*, 261(10):4377-4379 (1986).

Derynck et al., "Human transforming growth factor-β complementary DNA sequence and expression in normal and transformed cells", Nature, 316:701-705 (1985).

Derynck et al., "Sequence of the porcine transforming growth factor type B gene family", *Nucl. Acids Res.*, 15:3187 (1987).

Derynck et al., "Intron-exon structure of the human transforming growth factor-62 precurson gene", *Nucleic Acids Res.*, 15(7):3188-3189, (1987).

Dijke et al., "Identification of another member of the transforming growth factor type β gene family", *Proc. Natl. Acad. Sci.*, , 85:4715-4719 (1988).

(List continued on next page.)

Primary Examiner—Howard E. Schain
Assistant Examiner—P. Lynn Touzeau
Attorney, Agent, or Firm—Janet E. Hasak

[57] ABSTRACT

A method is provided for generation of bone at a site of an animal where skeletal tissue is deficient comprising administering to the animal, locally at the bone site in the presence of a source of osteogenic cells, an effective amount of a composition comprising TGF-β in a pharmaceutically acceptable carrier, provided that such composition excludes a bone morphogenetic cofactor, the composition being administered in an amount effective to induce bone growth at the bone site. Also provided is a device for implantation into a site of an animal where skeletal tissue is deficient comprising a device treated with an effective amount of a composition comprising TGF-β and a source of osteogenic cells in a pharmaceutically acceptable carrier.

3 Claims, 3 Drawing Sheets

OTHER PUBLICATIONS

Hanks, et al., "Amino acid sequence of the BSC-1 cell growth inhibitor (polyergin deduced from the nucleotide sequence of the cDNA", *Proc. Natl. Acad. Sci. USA*, 85:79–82 (1988).

Jakowlew et al., "Complementary Deoxyribonucleic Acid Cloning of a Novel Transforming Growth Factor β Messenger Ribonucleic Acid from chick Embryo Chondrocytes", *Mol. Endocrin.*, 2:747–755 (1988).

Jakowlew et al., "Complementary Deoxyribonucleic Acid Cloning of a Messenger Ribonucleic Acid Encoding Tranforming Growth Factor-β 4 from Chicken Embryo Chondrocytes", *Mol. Endocrin.*, 2:1186–1195.

Madisen et al., "Transforming Growth Factor-β2: cDNA Cloning and Sequence Analysis", *DNA*, 7(1):1–8, (1988).

Seyedin et al., "Cartilage–inducing Factor–A; Apparent Identity to Transforming Growth Factor-β", *Jour. Biological Chem.*, 261(13):5693–5695 (1986).

Seyedin et al., "Cartilage–inducing Factor–B Is a Unique Protein Structurally and Functionally Related to Transforming Growth Factor-β*", *Jour. Biological Chem.*, 262(5):1946–1949 (1987).

Sharples et al., "Cloning and Sequence Analysis of Simian Transforming Growth Factor-β cDNA", *DNA*, 6(3):239–244 (1987).

Stedman's Medical Dictionary, 24th ed. (Williams and Wilkins, Baltimore, Md. 1982) pp. 1054 and 1058.

Antosz and Aubin, J. Dent. Res., 67:235 (983) (1988).

Bauer et al., PNAS USA, 82:4132–4136 (1985).

Bentz t al., J. Cell. Biol., 107:162a (1989) 918 abstract.

Bentz et al., Development and Diseases of Cartilage and Bone Matrix, UCLA Symp. Mol. Cell. Biol., 137–147 (1987).

Bolander et al., New York Academy of Science, "Transforming Growth Factor βs Chemistry, Biology and Therapeutics, May 18–20, 1989.

Brown et al., N. Eng. J. Med., 321(2):76–79 (1989).

Burger et al., Calcif. Tiss. Int., 5–32 (F3).

Canalis et al., Calcif. Tiss. Int., 43:346–351 (1988).

Carrington et al., J. Cell Biol., 107:1969–1975 (1988).

Centrella et al., Endocrinology, 119:2306–2312 (1986).

Guenther et al., J. Bone and Min Res., 3(3)269–278 (1988).

Harrod et al., Calcif. Tiss. Int., 38: S16(62) (1985).

Centrella et al., FASEB J., 2:3066–3073 (1988).

Hauschka et al., J. Biol. Chem, 261:12665–12674 (1986).

Hayward and Fielder–Nagy, Agents & Actions, 22:251–254 (1987).

Centrella et al., J. Biol. Chem., 262:2869–2874 (1987).

Heine et al., J. Cell. Biol. 105:2861–2876 (1987).

Hiraki et al., Biochem & Biophys. Acta, 969:91–99 (1988).

Centrella et al., J. Cell Biol., 101:245a (930) (1985).

Hock et al., Calcif. Tiss. Int., 42: A32 (124) (1988).

Hollinger et al., J. Dent. Res., 68: 258(611) (1989).

Chenu et al., Calcif. Tiss. Int., 42:A10 (39) (1988).

Ibbotson et al., Devpmt & Diseases of Cartilage and Bone Matrix, UCLA Symp. Mol. Cell. Biol, 349–363 (1987).

Ibbotson et al., J. Bone & Min. Res., 4(1): 37–45 (1989).

Cotugno et al., J. Dental Res., 67:185 (581 (1988).

Ibbotson et al., J. Cell Biochem. Suppl, 10B:108 (1986) H15 abstract.

Ibbotson et al., PNAS USA, 83: 2228–2232 (1986).

D'Souza et al., J. Bone and Mineral Res., 1(1):74 (1986) 65 (abstract).

Ibbotson et al., Science, 221:1292–1994 (1983).

Edwards et al., EMBO J., 6(7): 1899–1904 (1987).

Elford et al., Bone, 8: 259–262 (1987).

Jennings et al., J. Cell Physiol., 137:167–172 (1988).

Globus et al., Endocrinol., 123:98–105 (1988).

Joyce et al., ASBMR/ICCRH Joint Meeting, 1989.

Kawamura and Urist, Dev. Biol., 130: 435–442 (1988).

Keski–Oja, J. Cell Biochem., 33(2): 95–107 (1987).

Komm et al., Science, 241: 81–84 (1988).

Linkhart et al., Bone, 7:479–487 (1986).

Mundy, J. Dent. Res., 67:108 (1988) (S47) abstract.

Mundy, J. NIH Res., 1: 65–68 (1989).

Noda and Camilliere, Endocrinology, 124:2991–2994 (1989).

Noda, Endocrinology, 124: 612–617 (1989).

Noda, J. Biol. Chem, 263: 13916–13921 (1988).

Noda et al., J. Cell Biol. 107: Dec. 1988, p. 48a, abstract No. 251.

Noda and Rodan, Biochem. Biophys. Res. Comm., 140:56–65 (1988).

Noda and Rodan, J. Cell. Physiol., 133: 426–437 (1987).

Oreffo et al., Calcified Tiss. Int., 42: Supp. A15 (1988).

Petkovich et al., J. Biol. Chem., 262: 13424–13428 (1987).

Pfeilschifter et al., Endocrinology, 121:212–218 (1987).

Pfeilschifter et al., J. Clin. Invest., 82: 680–685 (1988).

(List continued on next page.)

OTHER PUBLICATIONS

Pfeilschifter and Mundy, PNAS USA, 84: 2024–2028 (1987).
Robey et al., J. Cell Biol., 105:457–463 (1987).
Rodan et al., Calcif. Tiss. Int., 41: 14(OP10) (1987).
Rosen et al., J. Cell Biol., 103: 446a(1661) (1986).
Rosen et al., J. Cell Physiol. 134:337–346 (1988).
Rosen et al., NY Acad. Sci. Mtg., Abstr. TGF-β, May 18–20, 1989.
Russell, J. Dental. Res., 66: 99 (538) (Mar. 1987).
Sampath et al., PNAS USA, 84:7109–7113 (1987).
Sandberg et al., Development, 102: 461–470 (1988).
Sandberg et al., Devel, Biol., 130:324–334 (1988).
Schultz et al., Science, 235: 350–352 (1987).
Seyedin et al., J. Biol. Chem., 261: 5693–5695 (1986).
Seyedin et al., J. Biol. Chem., 262:1946–1949 (1987).
Seyedin et al., J. Cell Biochem. Supp., 10B:105 (H9) (1986).
Seyedin et al., PNAS USA, 82:2267–2271 (1985).
Terranova et al., J. Periodontol., Res., 22:248–251 (1987).
Terranova and Lyall, J. Periodontol., 57:311–317 (1986).
Terranova and Wikesjo, J. Periodontol., 58(6):371–380 (1987).
Uneno et al., J. Bone and Min. Res., 4(2):165–171 (1989).
Valentin-Opran et al., Rev. Rhum. Mal. Osteoartic, 51(11):627–632 (1984)–abstract.
Wang et al., PNAS USA, 85:9484–9488 (1988).
Wolf et al., Acta Endocrinol. Suppl., 120:(1) p. 242 (1989) 260 abstract.
Wozney et al., Science, 242:1528–1534 (1988).
Wrana et al., J. Cell Biol., 106:915–924 (1988).
Rosen et al., J. Cell Physiol., 134: 337–346 (1988).
Rosen, NY Acad. Sci. Mtg., Abstr. TGF-β, May 18–20, 1989.
Russell, J. Dental. Res., 66: 99 (538) (Mar. 1987).
Sanpath et al., PNAS USA, 84:7109–7113 (1987).
Sandberg et al., Development, 102:461–470 (1988).
Sandberg et al., Devel. Biol., 130:324–334 (1988).
Schultz et al., Science, 235:350–352 (1987).
Seyedin et al., J. Biol. Chem., 261:5693–5695 (1986).
Seyedin et al., J. Biol. Chem., 262:1946–1949 (1987).
Seyedin et al., J. Cell Biochem. Supp., 10B:105 (H9) (1986).
Seyedin et al., PNAS USA, 82:2267–2271 (1985).
Simpson, Trends Biochem Sci., 9:527–530 (1984).
Amman et al., NY Acad. Sci. Meeting (May 18, 1989).
Centrella et al., J. Cell Biol., 103:444a (1656) (1986).
Chenu et al., PNAS USA, 85:5683–5687 (1988).
Ignotz and Massague, J. Biol. Chem., 261:4337–4345 (1986).
Pfeilschifter et al., Acta Endocrinol. Supp., 120(1):144–145 (1989).
Pfeilschifter et al., Calcif. Tiss. Int., A34 (133).
Pfeilschifler and Mundy, Calcium Regulation & Bone Metabolism Basic and Clinical Aspects, Cohn et al., eds., 450–454 (1986).
Roberts et al., J. Cell Biol., 103(5): 1a–624a: p. 10a (1986) 34 abstract.
Roberts et al., Recent. Progress in Hormone–Res., 44:157–197 (1988).
Roberts and Sporn, Peptide Growth Factors and Their Receptors I, Handbook of Exp. Pharmacology. v. 951; Sporn, ed (1990), Ch. 8
Robey, Calcif. Tiss. Int., A34 (135).
Sodek et al., J. Dent. Res., 66: 191 (676) (1987).
Terek et al., Clin Res., 37(2):462A (1989).
Wakley et al., Non-Cemented Total Hip Arthroplasty, ed. Fitzgerald, Jr., 99–109, Chapter 17 (Raven Press, N.Y. 1988).

```
                        1            10            20           32         40          50
Hu TGF-β 1    MPPSGLRLLLPLLLPLLLWLLV-LTPGPPAAGLSTCKTIDMELVKRKRIEAIR
Hu TGF-β 2    MHYCVLSAFLILHLV--TVAL------S-LSTCSTLDMQFMRKRIEAIR
Hu TGF-β 3    --MHLQRALVVLALLNFATVSL------S-LSTCTTLDFGHIKKKRVEAIR 60           70           80           90
Hu TGF-β 1    GQILSKLRLASPPSQGE-VP-PGPLPEAVLALYNSTRDRVAGESAEPE-PE
Hu TGF-β 2    GQILSKLKLTSPP----EDYPEPEEVPPEVISIYNSTRDLL--QEKASR-RA
Hu TGF-β 3    GQILSKLRLTSPP----EPTV-MTHVPYQVLALYNSTRELL--EEHGER-KE
Ck TGF-β 4    -----------------------------------------M--DPMSIGPK- 100          110          120          130
Hu TGF-β 1    P------EADYYAKEVTRVLMV----ETHNEIYDKFKQSTHSIYMFFNTS
Hu TGF-β 2    AACERERSDEEYYAKEVYKIDMPPFFPS-EHAIPPTFYRPY-FRIVRFDVS
Hu TGF-β 3    EGCTQENTESEYYAKEIHKFDMIQGLAE-HNELAVCPKGIT-SKVFRFNVS
Ck TGF-β 4    -SCG--------------------GSPW-RPP-GTAPWSIG-SR--RATAS 140          150          160          170
Hu TGF-β 1    EL------RE-AVPEPVLLS-RAELRLLRLKL----KV-EQHVELYQ----
Hu TGF-β 2    A-------MEKNASNLV-KAEFRVFRLQNPK-ARVPEQRIELYQILKSK
Hu TGF-β 3    S-------VEKNRTNLF-RAEFRVLRVPNPS-SKRNEQRIELFQILRP-
Ck TGF-β 4    SSCSTSSRVRAEVGGRALLHRAELRMLRQKAAADSAGTEQRLELYQGYGN- 180          190          200          210         220
Hu TGF-β 1    KYSNNSWRYLSNRLLAPSDSPEWLSFDVTGVVRQWLSRGGEIEGFRLSAHC
Hu TGF-β 2    DLTSPTQRYIDSKVVKTRAEGEWLSFDVTDAVHEWLHHKDRNLGFKISLHC
Hu TGF-β 3    DEHIAKQRYIGGKNLPTRGTAEWLSFDVTDTVREWLLRRESNLGLEISIHC
Ck TGF-β 4    ----ASWRYLHGRSVRATADDEWLSFDVTDAVHQWLSGSELLGVFKLSVHC
Fg TGF-β 5    ----------------------SDEWMSFDVTKTVNEWLKRAEENEQFGLQPAC
```

FIG. 1A

```
                              230              240              250
Hu TGF-β 1  SC-------DSRDNTLQVDIN-GFTTGR------RGDLATI--------
Hu TGF-β 2  PCCTFVPSNNYIIPNKSEELEARFA-GIDGTSTYTSGDQKTIKSTRKKNSG
Hu TGF-β 3  PCHTFQP-NGDILENIHEVMEIKFK-GVDNEDDHGRGDLGRLK---KQKDH
Ck TGF-β 4  PCEMGPG-HADEMRISIEGFEQQ----------------RGDMQSIA----K-KHR
Fg TGF-β 5  KCPT-PQ-AKDI-D--IEGFPAL-----------------RGDLASLSS--KEN--

260              270              280              290
Hu TGF-β 1  HGMNRPFLLLMATPLERA-QH--LQSS----RHRRALDTNYCF--SSTEKNC
Hu TGF-β 2  KT----PHLLLMLLPSYRL-ESQ---QTNRRKKRALDAAYCF--RNVQDNC
Hu TGF-β 3  H--N-PHLILMMIPPHRL-DNPGQGGQ---RKKRALDTNYCF--RNLEENC
Ck TGF-β 4  R---V-PYVLAMALPAERANE---LHSA----RRRRDLDTDYCFGPGTDEKNC
Fg TGF-β 5  -TK--PYL--MIT-SMPAERIDTVTSS---RKKRGVGQEYCF--GNNGPNC 300              310              320              330              340
Hu TGF-β 1  CVRQLYIDFRKDLGWKWIHEPKGYHANFCLGPCPYIWSLDTQYSKVLALYN
Hu TGF-β 2  CLRPLYIDFKRDLGWKWIHEPKGYNANFCAGACPYLWSSDTQHSRVLSLYN
Hu TGF-β 3  CVRPLYIDFRQDLGWKWVHEPKGYYANFCSGPCPYLRSADTTHSTVLGLYN
Ck TGF-β 4  CVRPLYIDFRKDLGWKWIHEPKGYMANFCMGPCPYIWSADTQYTKVLALYN
Fg TGF-β 5  CVKPLYINFRKDLGWKWIHEPKGYEANYCLGNCPYIWSMDTQYSKVLSLYN 350              360              370              380              390
Hu TGF-β 1  QHNPGASAAPCCVPQALEPLPIVYYVGRKPKVEQLSNMIVRSCKCS
Hu TGF-β 2  TINPEASASPCCVSQDLEPLTILYYIGKTPKIEQLSNMIVKSCKCS
Hu TGF-β 3  TLNPEASASPCCVPQDLEPLTILYYVGRTPKVEQLSNMVVKSCKCS
Ck TGF-β 4  QHNPGASAAPCCVPQTLDPLPIIYYVGRNVRVEQLSNMVVRACKCS
Fg TGF-β 5  QNNPGASISPCCVPDVLEPLPIIYYVGRTAKVEQLSNMVVRSCNCS
```

TGF-β COMPOSITION FOR INDUCING BONE GROWTH

This application is a continuation of application Ser. no. 08/063,841, filed on 18 May 1993, which is a continuation of application Ser. no. 07/790,856, filed on 12 Nov. 1991, now abandoned, which is a divisional of application Ser. no. 07/401,906, filed on 1 Sep. 1989, now U.S. Pat. No. 5,158,934.

BACKGROUND OF THE INVENTION

1. Field of the Invention

This invention relates to the use of transforming growth factor-beta to induce bone growth in vivo and to devices for implantation into a bony site that are treated with transforming growth factor-beta, as well as to pharmaceutical compositions for this purpose.

2. Description of Related Art

The disorders associated with bone loss present major public health problems for Western societies. Osteoporosis alone may affect 20 million Americans in the early years of the next century. Hence, there is wide interest in identifying factors or potential therapeutic agents that inhibit bone loss and stimulate the formation of healthy new bone.

Bone is an extremely complex, but highly organized, connective tissue that is continuously remodeled during the life of an adult by cellular events that initially break it down (osteoclastic resorption) and then rebuild it (osteoblastic formation). This remodeling process occurs in discrete packets throughout the skeleton, i.e., in both cortical bone and trabecular bone. It has recently been reported that mouse bone marrow cells can be stimulated to generate osteoclasts in the presence of parathyroid hormone-related protein or vitamin D. See Akatsu et al., *Endocrinology*, 125: 20-27 (1989); Takahashi et al., *Endocrinology*, 123: 2600-2602 (1988) and Takahashi et al., *Endocrinology*, 123: 1504-1510 (1988).

The currently available therapeutic agents known to stimulate bone formation are fluoride, estrogen, metabolites, and vitamin D. Fluoride clearly increases trabecular bone mass, but questions remain about the quality of the new bone formed, the side effects observed in some patients, whether there are beneficial effects on vertebral fracture rates, and whether increased fragility of cortical bone with subsequent propensity to hip fracture follows.

Another approach is using agents that promote resorption (parathyroid hormone) and then interrupt resorption (calcitonin). One proposed, but not validated, such sequential therapeutic regimen is coherence therapy, where bone metabolic units are activated by oral phosphate administration and then resorption is inhibited by either diphosphonates or calcitonin.

Within the past few years several factors that stimulate osteoblasts were identified in bone, including TGF-β, fibroblast growth factor, platelet-derived growth factor, insulin-like growth factor I, and β2 macroglobulin. Of these, TGF-β and IGF-I were deemed attractive candidates for factors linking previous bone resorption with subsequent bone formation. Mundy, *The Journal of NIH Research*, 1: 65-68 (1989).

Other proteins stored in the bone matrix may also be important for bone formation. When demineralized bone was injected into the muscle or subcutaneous tissue of rats, a cascade of events, including chondrogenesis, ensued. Urist, *Science*, 150: 893 (1965). This observed activity was due to bone morphogenetic protein (BMP). Since the 1960s several investigators have attempted to identify and characterize this activity. Thus, a protein of 22 Kd, called osteogenin, was identified that possessed the activity. Sampath et al., *Proc. Natl. Acad, Sci. U.S.A.*, 84: 7109 (1987). Recently, a glycoprotein called osteoinductive factor was purified that exhibited many of the same properties as TGF-β in vitro but which, unlike TGF-β, could induce all of the events involved in the osteoinductive process in vivo. Bentz et al., *J. Cell. Biol.*, 107: 162a (1989). Additionally, three proteins from demineralized ovine bone matrix were identified as having this activity. Wang et al., *Proc. Natl. Acad. Sci.*, 85: 9484 (1988) and Wozney et al., *Science*, 242: 1528 (1988). These proteins were named BMP-1, BMP-2A, and BMP-3, the latter two of which belong to the extended TGF-β family by limited sequence homology. These workers modified the assay for bone induction to show cartilage formation but did not show that the proteins ultimately stimulate formation of bone.

The transforming growth factor-beta (TGF-β) group of molecules are each dimers containing two identical polypeptide chains linked by disulfide bonds. The molecular mass of these dimers is about 25 Kd. Biologically active TGF-β has been defined as a molecule capable of inducing anchorage-independent growth of target cell lines or rat fibroblasts in in vitro cell culture, when added together with EGF or TGF-α as a co-factor. TGF-β is secreted by virtually all cell types in an inactive form. This latent form can be activated by proteolytic cleavage of mature TGF-β from its precursor (at the Arg-Ala bond in position 278). A non-covalent complex is formed from the association of the mature TGF-β with the precursor remainder or with a protein binding to TGF-β or with alpha$_2$-macroglobulin. This complex is disrupted so as to activate the TGF-β either by exposure to transient acidification or by the action of exogenous proteases such as plasmin or plasminogen activator.

There are at least five forms of TGF-β currently identified, TGF-β1, TGF-β2, TGF-β3, TGF-β4, and TGF-β5. Suitable methods are known for purifying this family of TGF-βs from various species such as human, mouse, green monkey, pig, bovine, chick, and frog, and from various body sources such as bone, platelets, or placenta, for producing it in recombinant cell culture, and for determining its activity. See, for example, R. Derynck et al., *Nature*, 316: 701-705 (1985); European Pat. Pub. Nos. 200,341 published Dec. 10, 1986, 169,016 published Jan. 22, 1986, 268,561 published May 25, 1988, and 267,463 published May 18, 1988; U.S. Pat. No. 4,774,322; Seyedin et al, *J. Biol. Chem.*, 262: 1946-1949 (1987); Cheifetz et al, *Cell*, 48: 409-415 (1987); Jakowlew et al., *Molecular Endocrin.*, 2: 747-755 (1988); Dijke et al., *Proc. Natl. Acad., Sci. (U.S.A.)*, 85: 4715-4719 (1988); Derynck et al., *J. Biol. Chem.*, 261: 4377-4379 (1986); Sharples et al., *DNA*, 6: 239-244 (1987); Derynck et al., *Nucl. Acids Res.*, 15: 3188-3189 (1987); Derynck et al., *Nucl. Acids. Res.*, 15: 3187 (1987); Derynck et al., EMBO J., 7: 3737-3743 (1988)); Seyedin et al., *J. Biol. Chem.*, 261: 5693-5695 (1986); Madisen et al., *DNA*, 7: 1-8 (1988); and Hanks et al., *Proc. Natl. Acad. Sci.* (U.S.A.), 85: 79-82 (1988), the entire contents of these publications being expressly incorporated by reference.

TGF-β3, TGF-β4, and TGF-β5, which are the most recently discovered forms of TGF-β, were identified by screening cDNA libraries. None of these three putative proteins has been isolated from natural sources, although Northern blots demonstrate expression of the corresponding mRNAs. TGF-$\beta$4 and TGF-$\beta$5 were cloned from a chicken chondrocyte cDNA library (Jakowlew et al., *Molec. Endocrinol.*, 2: 1186–1195 (1988)) and from a frog oocyte cDNA library, respectively. The frog oocyte cDNA library can be screened using a probe derived from one or more sequences of another type of TGF-$\beta$. TGF-$\beta$4 mRNA is detectable in chick embryo chondrocytes, but is far less abundant than TGF-$\beta$3 mRNA in developing embryos or in chick embryo fibroblasts. TGF-$\beta$5 mRNA is expressed in frog embryos beyond the neurula state and in Xenopus tadpole (XTC) cells.

TGF-$\beta$ has been shown to have numerous regulatory actions on a wide variety of both normal and neoplastic cells. TGF-$\beta$ is multifunctional, as it can either stimulate or inhibit cell proliferation, differentiation, and other critical processes in cell function (M. Sporn, *Science*, 233:532 [1986]). For a general review of TGF-$\beta$ and its actions, see Sporn et al., *J. Cell Biol.*, 105: 1039–1045 (1987) and Sporn and Roberts, *Nature*, 332: 217–219 (1988).

The multifunctional activity of TGF-$\beta$ is modulated by the influence of other growth factors present together with the TGF-$\beta$. TGF-$\beta$ can function as either an inhibitor or an enhancer of anchorage-independent growth, depending on the particular set of growth factors, e.g., EGF or TGF-$\alpha$, operant in the cell together with TGF-$\beta$ (Roberts et al., *Proc. Natl. Acad. Sci. U.S.A.*, 82:119 [1985]). TGF-$\beta$ also can act in concert with EGF to cause proliferation and piling up of normal (but not rheumatoid) synovial cells (Brinkerhoff et al., *Arthritis and Rheumatism*, 26:1370 [1983]).

Although TGF-$\beta$ has been purified from several tissues and cell types, as indicated above, it is especially abundant in bones (Hauschka et al., *J. Biol. Chem.*, 261: 12665 (1986)) and platelets (Assoian et al., *J. Biol. Chem.*, 258: 7155 (1983)). TGF-$\beta$ is postulated to be one of the local mediators of bone generation and resorption, because of its presence in large amounts in bone and cartilage, because cells with osteoblast and chondrocyte lineage increase replication after exposure to TGF-$\beta$, and because TGF-$\beta$ regulates differentiation of skeletal precursor cells. See Centrella et al., *Fed. Proc. J.*, 2: 3066–3073 (1988).

Immunohistochemical studies have shown that TGF-$\beta$ is involved in the formation of the axial skeleton of the mouse embryo. TGF-$\beta$ is also present in other embryos in the cytoplasm of osteoblasts in centers of endochondral ossification and in areas of intramembranous ossification of flat bones, such as the calvarium. Heine et al., *J. Cell Biol.*, 105: 2861–2876 (1987). Following in situ hybridization of TGF-$\beta$1 probes, localization of TGF-$\beta$ in both osteoclasts and osteoblasts has been described in development of human long bones and calvarial bones. Sandberg et al., *Development*, 102: 461–470 (1988), Sandberg et al., *Devel. Biol.*, 130: 324–334 (1988). TGF-$\beta$ is found in adult bone matrix (Seyedin et al., *Proc. Natl. Acad. Sci. U.S.A.*, 82: 2267–2271 (1985), Seyedin et al., *J. Biol. Chem.*, 261: 5693–5695 (1986)) and appears at the time of endochondral ossification in an in vivo model of bone formation (Carrington et al., *J. Cell. Biol.*, 107: 1969–1975 (1988)). Cultured fetal bovine bone osteoblasts as well as rat osteosarcoma cells have high mRNA levels for TGF-$\beta$ and secrete relatively high concentrations of TGF-$\beta$ (Robey et al., *J. Cell. Biol.*, 105: 457–463 (1987)).

In certain in vitro models, TGF-$\beta$ was found to stimulate the synthesis of collagen, osteopontin, osteonectin, and alkaline phosphatase, and to stimulate replication in osteoblast-like cells. See Centrella et al., *J. Biol. Chem.*, 262: 2869–2874 (1987), Noda et al., J., *Biol. Chem.*, 263: 13916 (1988), Wrana et al., *J. Cell. Biol.*, 106: 915 (1988), Noda et al., *J. Cell. Physiol.*, 133: 426 (1987), Pfeilshifter et al., *Endocrinology*, 121: 212 (1987), Centrella et al., *Endocrinology*, 119: 2306 (1986), and Roby et al., *J. Cell. Biol.*, 105: 457 (1987). In other in vitro models, TGF-$\beta$ was found to inhibit proliferation and expression of alkaline phosphatase and osteocalcin. See Centrella et al., supra, Noda and Rodan, *Biochem. Biophys. Res. Commun.*, 140: 56 (1986), and Noda, *Endocrinology*, 124: 612 (1989).

Further, while Centrella et al., supra, showed increased collagen synthesis after treatment of osteoblasts from rat calvaria with TGF-$\beta$, Robey et al., supra, could not show increased synthesis of collagen in fetal bovine bone osteoblasts, postulating that the increased collagen production is secondary to the effects of TGF-$\beta$ on the proliferation of osteoblasts. In organ culture, TGF-$\beta$ was reported to stimulate bone resorption in neonatal mouse calvarias, but inhibit resorption in the fetal rat long bone system. See Tashjian et al., *Proc. Natl. Acad. Sci. U.S.A.*, 82: 4535 (1981) and Pfeilshifter et al., *J. Clin. Invest.*, 82: 680 (1988). TGF-$\beta$ activity was reported to be increased in cultures of fetal rat calvaria and in calvarial cells incubated with stimulators of bone resorption, such as parathyroid hormone, 1,25-dihydroxyvitamin $D_3$, and IL-1 (Petkovich et al., *J. Biol. Chem.*, 262: 13424–13428 (1987), Pfeilschifter and Mundy, *Proc. Natl. Acad. Sci. U.S.A.*, 84: 2024–2028 (1987)). Furthermore, it was reported that TGF-$\beta$ inhibits the formation of osteoclasts in bone marrow cultures. Chenu et al., *Proc. Natl. Acad. Sci. U.S.A.*, 85: 5683–5687 (1988). The showing that TGF-$\beta$ has effects on both osteoclasts and osteoblasts led Pfeilschifter and Mundy, supra, to propose that it is involved in the strict coupling of the processes of bone resorption and bone formation characteristic of the remodeling process in adult bone. It has also been postulated that the local acidic, proteolytic environment provided by the osteoclasts results in activation of matrix-associated latent TGF-$\beta$. Oreffo et al., *Calcified Tiss. Internatl.*, 42: Suppl:A15 (1988).

In view of the conflicting results reported for in vitro activities, it is not clear whether in vitro models can be used to predict the effects of TGF-$\beta$ on bone formation and resorption in vivo. See Roberts et al., *Proc. Natl. Acad. Sci. U.S.A.*, 82: 119 (1985).

Additional references reporting that TGF-$\beta$ promotes the proliferation of connective and soft tissue for wound healing applications include U.S. Pat. No. 4,810,691 issued Mar. 7, 1989, U.S. Pat. No. 4,774,228 issued Sep. 27, 1988, Ignotz et al., *J. Biol. Chem.*, 261:4337 [1986]; J. Varga et al., *B. B. Res. Comm.*, 138:974 [1986]; A. Roberts et al., *Proc. Natl. Acad. Sci. U.S.A.*, 78:5339 [1981]; A. Roberts et al., *Fed. Proc.*, 42:2621 [1983]; and U.S. Pat. No. 4,774,228 to Seyedin et al. TGF-$\beta$ stimulates the proliferation of epithelia (T. Matsui et al., *Proc. Natl. Acad. Sci. U.S.A.*, 83:2438 [1986]; G. Shiplay et al. *Cancer Res.*, 6:2068 [1986]); induces collagen secretion in human fibroblast cultures (Chua et al., *J. Biol. Chem.*, 260:5213–5216 [1983]); stimulates the release of prostaglandins and mobilization of calcium (A. Tashjian et al., *Proc. Natl. Acad. Sci.*

U.S.A., 82:4535 [1985]); and inhibits endothelial regeneration (R. Heimark et al., Science, 233:1078 [1986]).

In wound chambers implanted subcutaneously, TGF-$\beta$ increased DNA and collagen production. Sporn et al., Science, 219:1329 (1983) and Sprugel et al., Am. J. Pathol., 129: 601 (1987). Moreover, TGF-$\beta$ produced collagen fibrosis when injected subcutaneously (Roberts et al., Proc. Natl. Acad. Sci. U.S.A., 83: 4167-4171 (1986)) and promoted healing of skin incisions in rats (Mutoe et al., Science, 237: 1333 (1987)). Nevertheless, although TGF-$\beta$ induced chondrogenesis in muscle-derived cells in vitro (Seyedin et al., Proc. Natl. Acad. Sci. U.S.A., 82: 2267 (1985) and Seyedin et al., J. Biol. Chem., 261: 5693 (1986)), it did not produce cartilage in vivo even when implanted with collagenous substrates, a system used for a long time as a bone induction model in animals (Sampath et al., Proc. Natl, Acad. Sci. U.S.A., 84: 7109 (1987) and Howes et al., Calcif. Tissue Int., 42: 34 (1988)).

New studies have shown a time-dependent appearance of mRNA for TGF-$\beta$1 at a fracture site in a rat and have localized the peptide immunohistochemically in the periosteum of the healing fracture; the same researchers reported that injections of TGF-$\beta$1 into the periosteal area of the femur of young rats have caused significant formation of new cartilage. Bolander et al., New York Academy of Sciences, "Transforming Growth Factor-$\beta$s: Chemistry, Biology and Therapeutics, May 18-20, 1989. It has been found that injections of TGF-$\beta$1 into the parietal bone of young rats stimulated periosteal bone formation, resulting in a thickening of the calvarium. Node et el., J. Cell. Biol., 107: 48 (1988). TGF-$\beta$ was reported to stimulate local periosteal woven bone formation when injected daily onto the periostea of parietal bones of neonatal rats. Node and Camilliere, Endocrinology, 124: 2991-2994 (1989).

Certain researchers have found that TGF-$\beta$ does not induce bone formation unless it is administered concurrently with a cofactor, e.g., an osteoinductive factor purified from bovine demineralized bone. Bentz et al., supra, Seyedin et al. U.S. Pat. No. 4,843,063 issued Jun. 27, 1989, and U.S. Pat. No. 4,774,322 issued Sep. 27, 1988.

The above studies are inconclusive and inconsistent regarding the formation of mature, histologically normal bone with TGF-$\beta$ alone. For example, the bones being generated by Noda et al., 1989, supra, were neonatal, i.e., not fully formed with large spaces and increased cartilage formation. In addition, woven bone is resorbed before mature bone is laid down. Thus there is still a demonstrated need for a bone induction agent that will induce bone only where it is needed, does not have side effects in some patients as does fluoride treatment, and does not require addition of a cofactor or another peptide growth factor for acceleration of repair of damaged bone in vivo.

Accordingly, it is an object of the present invention to provide exogenous TGF-$\beta$ to a local site on an animal where skeletal (bony) tissue is deficient without administering a bone-inducing cofactor so as to produce in every case mature, morphologically normal bone at the site of administration where it is needed.

It is another object to provide a device for implantation into an animal for generation of bone that is treated with TGF-$\beta$ in such a way as to induce bone at the implantation site.

These and other objects will become apparent to those skilled in the art.

SUMMARY OF THE INVENTION

The above objects are achieved by providing a method for generation of bone at a site of an animal where skeletal tissue is deficient comprising administering to the animal, locally at the site in the presence of an osteogenic cell source, an effective amount of a composition comprising TGF-$\beta$ in a pharmaceutically acceptable carrier, provided that such composition excludes a bone morphogenetic cofactor, the composition being administered in an amount effective to induce bone growth at the site.

In another aspect, the invention provides a device for implantation into a site of an animal where skeletal tissue is deficient comprising a device treated with an effective amount of a composition comprising TGF-$\beta$ and an osteogenic cell source in a pharmaceutically acceptable carrier.

In a still further aspect, the invention provides a pharmaceutical composition for treatment of a site of an animal where skeletal tissue is deficient comprising an effective amount of TGF-$\beta$ and an osteogenic cell source in a pharmaceutically acceptable carrier.

These aspects of the invention enable the generation of normal mature bone every time only where it is required at a particular site, without having to add a specific bone-inducing cofactor to ensure bone formation. Preclinical results with TGF-$\beta$ applied topically as described below show new bone formation in the presence of perichondrium in a rabbit, new bone formation surrounding ceramic implants in bone defects in a rat, and bone formation in a primate.

DESCRIPTION OF THE PREFERRED EMBODIMENTS

A. Definitions

By "inducing bone growth" is meant promoting the formation of morphologically normal, mature bone only at a site where there is a bone deficiency that needs to be replaced. Mature bone is bone of any type, whether cortical or trabecular, that is mineralized as opposed to immature or cartilaginous bone as would be formed in a neonatal model. Morphologically normal bone is bone that is detected histologically as normal (i.e., consisting of endochondral or membranous type lamellar bone and including marrow spaces with osteoblasts and osteoclasts). This is in contrast, for example, to callous formation with a fibrotic matrix as seen in the first stage of fracture healing. Thus, the bone induction herein is contemplated not only as acceleration of bone regeneration, as in a fracture, but also as stimulation of the formation of bone that is returned to its normal morphological state.

By "skeletal tissue deficiency" is meant a deficiency in bone at any site where it is desired to restore the bone, no matter how bone deficiency originated, e.g., whether as a result of surgical intervention, removal of tumor, ulceration, implant, or fracture.

By "bone morphogenetic cofactor" is meant a protein originally found in the bone matrix that induces all of the cascade events involved in the osteoinductive process in vivo, including chondrogenesis, vascular invasion, formation of a marrow cavity, and eventually formation of a bone ossicle. Such factors include the bone morphogenetic proteins as found in demineralized bone (Urist, *Science*, 150: 893 (1965)), osteogenin, a 22 Kd protein with this activity (Sampath et al., *Proc. Natl. Acad. Sci. U.S.A.*, 84: 7109 (1987)), a glycoprotein called osteoinductive factor (U.S. Pat. No. 4,843,063, supra), and BMP-1, BMP-2A, and BMP-3 from demineralized ovine bone matrix (Wang et al, *Proc. Natl. Acad. Sci. U.S.A.*, 85: 9484 (1988) and Wozney et al., *Science*, 242: 1528 (1988)), the disclosures of all of which references are incorporated herein by reference.

The osteoinductive cofactor described in the U.S. patent is isolated from bone, preferably a bovine metatarsal bone, wherein the demineralized bone is prepared, noncollagenous proteins are extracted from the bone, the extract is subjected to gel filtration, the fraction constituting a low molecular weight (10,000–40,000 daltons) possessing the greatest chondrogenic activity is subjected to ion-exchange chromatography, the first fraction CM-1 is subjected to RP-HPLC, and two peaks of predominantly 28 Kd and 36 Kd chondrogenic/osteogenic cofactor protein are purified to give single bands on SDS-PAGE. These cofactors and the others mentioned above are included in the term "bone morphogenetic cofactor."

By "osteogenic cell source" is meant a source of viable cells that are capable of forming bone, as well as viable cells that are precursors to cells capable of forming bone. Suitable such sources include dispersed whole bone marrow cells (obtained by, e.g., aspiration or mechanical agitation), perichondrium, periosteum, or a suitable cell line. For example, the cells may be taken from a site of the animal to be treated adjacent to the deficiency (e.g., periosteum stripped from an adjacent site to the defect such as a fracture site or a surgical excision site) or from a biopsy site of the animal (e.g., one that has been previously accessed, e.g., the hip).

By "animal" is meant any animal having a vertebrate structure, preferably a mammal, and most preferably a human.

By "TGF-$\beta$" is meant the family of molecules described hereinabove that have either the full-length, native amino acid sequence of any of the TGF-$\beta$s from any species, including the latent forms and associated or unassociated complex of precursor and mature TGF-$\beta$ ("latent TGF-$\beta$"). Reference to such TGF-$\beta$ herein will be understood to be a reference to any one of the currently identified forms, including TGF-$\beta$1, TGF-$\beta$2, TGF-$\beta$3, TGF-$\beta$4, and TGF-$\beta$5 and latent versions thereof, as well as to TGF-$\beta$ species identified in the future, including polypeptides derived from the sequence of any known TGF-$\beta$ and being at least 75% homologous with the sequence. Members of the TGF-$\beta$ family are defined as those which have nine cysteine residues in the mature portion of the molecule, share at least 65% homology with other known TGF-$\beta$ sequences in the mature region, and compete for the same receptor. In addition, they all appear to be encoded as a larger precursor that shares a region of high homology near the N-terminus and shows conservation of three cysteine residues in the portion of the precursor that will later be removed by processing. Moreover, the TGF-$\beta$s appear to have a four or five amino acid processing site.

B. Modes for Carrying Out the Invention

The invention is carried out in one aspect by mixing the TGF-$\beta$ with a suitable pharmaceutical carrier, and without the bone morphogenetic cofactor, and administering the resulting composition locally to a site on an animal where it is desired to induce formation of normal, adult bone and where a source of osteogenic cells and their precursor cells are present at the site. If the site does not naturally have a source of osteogenic cells present, the pharmaceutical composition also contains an osteogenic cell source as defined above, in an Mount sufficient to induce bone growth.

Examples of indications where promotion of bone repair at a skeletal site is important include periodontal disease where root socket healing is impaired (tooth socket sites), non-union fractures, including primary treatment of high risk fractures and adjunctive treatment with bone grafting or bone substitutes for established non-union fractures, large bony defects caused by trauma or surgery [e.g., partial mandibular resection for cancer, large cranial defects, spinal (vertebral) fusions, correction of severe scoliosis by surgical alignment held in place with a Harrington bar (to shorten the six months normally required for a body cast), and spinal fractures with open reduction (to decrease significantly the period of immobilization)], and rapid stabilization and enhanced fixation of artificial prostheses and spacer bars, oral joints, and bone replacements.

Examples of the latter include plastic and reconstructive surgery, fixation of permanent dentures into mandible, enhanced fixation of accepted joint prosthesis, e.g., hips, knees, and shoulders (leading to the acceptance of prostheses that until now have been unacceptable due to rapid loosening and instability such as elbows), and limb salvage procedures, usually associated with malignancy (the bone shaft may be removed but the articular surfaces are left in place and connected by a space bar; rapid and enhanced fixation is required for success). If the site constitutes a periodontal site, i.e., one that involves the teeth, gums, and dental sockets, the TGF-$\beta$ is administered in conjunction with an exogenously added source of osteogenic cells.

In one preferred embodiment, the TGF-$\beta$ is administered by treating a device with the TGF-$\beta$ composition and implanting the device into the animal at the site of the deficiency, the composition also containing the osteogenic cell source when the site is deficient in such cells. The device may consist of any device suitable for implantation, including a molded implant, plug, prosthetic device, capsule, titanium alloy, sponge, or ceramic block. Examples of suitable delivery vehicles useful as devices are those disclosed by Nade et al., *Clin. Orthop. Rel. Res.*, 181: 255–263 (1982); Uchida et al., *J. Biomed. Mat. Res.*, 21: 1–10 (1987); Friedenstein et al., *Exp. Hematol.*, 10: 217–227 (1982); Deporter et al., *Calcif. Tissue Int.*, 42: 321–325 (1988); McDavid et al., *J. Dent. Res.*, 58: 478–483 (1979); Ohgushi et al., *J. Orthopaedic Res.*, 7: 568–578 (1989), Aprahamian et al., *J. Biomed. Mat. Res.*, 21: 965–977 (1986); Emmanual et al., *Stain. Tech.*, 62: 401–409 (1987), the disclosure of all of which references is incorporated herein by reference.

For bone defects involving gaps, such as a dry socket or non-union fracture, a plug may be used to fill the gap. The plug may be composed of, for example, hydroxyapatite or collagen on which TGF-$\beta$ is adsorbed. For larger bone defects resulting from, e.g., trauma or skeletal reconstruction around an ulcer or hip prosthesis, the device is preferably a made-to-fit ceramic block. More preferably, the ceramic block comprises 0-100% hydroxyapatite and the remaining 100-0% tricalcium phosphate, by weight, most preferably 60% hydroxyapatite and 40% tricalcium phosphate.

In a specific embodiment for a jaw implant, a calcium carbonate moldable material or Interpore TM molding device is molded to fit the jaw using a 3-dimensional x-ray of the jaw before surgery, and the molded material is impregnated with TGF-$\beta$. Then, dispensed bone marrow from another site of the animal (e.g., from the hip) is infiltrated into the mold, and the mold is placed into the jaw for final implantation.

Preferably, the device is treated with the TGF-$\beta$ composition (which includes both a solution and a gel formulation) for a sufficient period of time to allow adsorption, and to allow drying in the case of the gel. The concentration of TGF-$\beta$ in the solution or gel and the time of exposure depend on a number of factors, including the volume of the defect, the potency of the TGF-$\beta$ polypeptide, and the nature of the site to which it is applied, and will be adjusted accordingly. As the size of the defect increases, or when the site is other than a bone site, the concentration of TGF-$\beta$ and the time of presoaking should be increased. The treatment is for preferably at least about 0.5 hour, depending on the factors mentioned above (more preferably at least about 1 hour, and most preferably 1-2 hours), before implantation. Also depending on the above considerations, the concentration of TGF-$\beta$ in the TGF-$\beta$ composition is preferably at least about 1 ng/ml (more preferably at least about 1-10 up to 100 ng/ml). The treatment may consist of any mode by which the composition is applied to the device to deliver effectively the TGF-$\beta$ and the osteogenic cell source. Such treatment includes, for example, adsorption, covalent crosslinking, or impregnation, depending in part on the nature of the indication.

The TGF-$\beta$ compositions to be used in the therapy will be dosed in a fashion consistent with good medical practice taking into account the nature of the skeletal tissue deficiency to be treated, the species of the host, the medical condition of the individual patient, the presence of any other cotreatment drug in the composition, the site of delivery of the agent, the method of administration, the scheduling of administration, and other factors known to practitioners. Because of differences in host response, significant site-to-site and patient-to-patient variability exists. For purposes herein, the "therapeutically effective amount" of TGF-$\beta$ is an amount that is effective to induce bone growth, as defined above, at the site of skeletal tissue deficiency.

As a general proposition, the TGF-$\beta$ is formulated and delivered to the target site at a dosage capable of establishing at the site a TGF-$\beta$ level greater than about 0.1 ng/cc. Typically, the TGF-$\beta$ concentrations range from about 0.1 ng/cc to 5 mg/cc, preferably from about 1 to 2000 ng/cc. These intra-tissue concentrations are maintained preferably by topical application and/or sustained release.

As noted above, these suggested amounts of TGF-$\beta$ are subject to a great deal of therapeutic discretion. The key factor in selecting an appropriate dose and scheduling is the result obtained. Clinical parameters to determine an endpoint include increase in bone formation and mass and in radiographically detectable bone height. Such measurements are well known to those clinicians and pharmacologists skilled in the art.

The TGF-$\beta$ composition is administered by any suitable means locally to the site, including topical and continuous release formulation. The active TGF-$\beta$ ingredient is generally combined at ambient temperature at the appropriate pH, and at the desired degree of purity, with a physiologically acceptable carrier, i.e., a carrier that is non-toxic to the patient at the dosages and concentrations employed. The carrier may take a wide variety of forms depending on the form of preparation desired for administration.

To be effective, the TGF-$\beta$ is converted by the body to its activated form, i.e., the mature form is cleaved from its precursor using a suitable enzyme and the resultant complex is treated with acid or other appropriate agent, to activate the TGF-$\beta$. Nevertheless, TGF-$\beta$ is suitably administered in an inactive or delayed release form such as a complex of mature TGF-$\beta$ with proTGF-$\beta$ not containing mature TGF-$\beta$ (i.e., the remaining precursor of TGF-$\beta$), with a TGF-$\beta$ binding protein, or with alpha$_2$-macroglobulin. The latent form is then converted to the active form either by naturally occurring mechanisms in the local environment or by formulation with TGF-$\beta$ activating agents described above. See, e.g., Gentry et al., *Mol. Cell. Biol.*, 8: 4162-4168 (1988); Miyazono et al., *J. Biol. Chem.*, 263: 6407-6415 (1988); Wakefield et al., *J. Biol. Chem.*, 263: 7646-7654 (1988); Keski-Oja et al., *J. Cell Biochem. Suppl.*, 11A: 60 (1987); Kryceve-Martinerie et al., *Int. J. Cancer*, 35:553-558 (1985); Lawrence et al., *Biochem. Biophys. Res. Commun.*, 133: 1026-1034 (1985); Lawrence et al., *J. Cell Physiol.*, 121: 184-188 (1984). Thus, the pH of the TGF-$\beta$ composition may suitably reflect the conditions necessary for activation.

For the preparation of a liquid composition suitable for impregnation of a device, the carrier is suitably a buffer, a low molecular weight (less than about 10 residues) polypeptide, a protein, an amino acid, a carbohydrate including glucose or dextran, a chelating agent such as EDTA, a cellulose, or other excipient. In addition, the TGF-$\beta$ composition is preferably sterile. Sterility is readily accomplished by sterile filtration through (0.2 micron) membranes. TGF-$\beta$ ordinarily will be stored as an aqueous solution, as it is highly stable to thermal and oxidative denaturation, although lyophilized formulations for reconstitution are acceptable.

Generally, where the bone disorder permits, one should formulate and dose the TGF-$\beta$ for site-specific delivery, where the TGF-$\beta$ is formulated into a sterile sustained-release composition suitable for local application to the desired site.

For local application of the TGF-$\beta$ composition, for example, in the case of a bone defect that is a crack, e.g., a union fracture, the carrier may be any vehicle effective for this purpose. For obtaining a gel formulation, the liquid composition is typically mixed with an effective Mount of a water-soluble polysaccharide, polyethylene glycol, or synthetic polymer such as polyvinylpyrrolidone to form a gel of the proper viscosity to be applied topically. The polysaccharide is generally present in a gel formulation in the range of 1-90% by weight of the gel, more preferably 1-20%. Examples of other suitable polysaccharides for this purpose, and a determination of the solubility of the polysaccharides, are found in EP 267,015, published May 11, 1988, the disclosure of which is incorporated herein by reference.

The polysaccharide that may be used includes, for example, cellulose derivatives such as etherified cellulose derivatives, including alkyl celluloses, hydroxyalkyl celluloses, and alkylhydroxyalkyl celluloses, for example, methylcellulose, hydroxyethyl cellulose, carboxymethyl cellulose, hydroxypropyl methylcellulose, and hydroxypropyl cellulose; starch and fractionated starch; agar; alginic acid and alginates; gum arabic; pullullan; agarose; carrageenan; dextrans; dextrins; fructans; inulin; mannans; xylans; arabinans; chitosans; glycogens; glucans; and synthetic biopolymers; as well as gums such as xanthan gum; guar gum; locust bean gum; gum arabic; tragacanth gum; and karaya gum; and derivatives and mixtures thereof. The preferred gelling agent herein is one that is inert to biological systems, nontoxic, simple to prepare, and not too runny or viscous, and will not destabilize the TGF-$\beta$ held within it.

Preferably the polysaccharide is an etherified cellulose derivative, more preferably one that is well defined, purified, and listed in USP, e.g., methylcellulose and the hydroxyalkyl cellulose derivatives, such as hydroxypropyl cellulose, hydroxyethyl cellulose, and hydroxypropyl methylcellulose. Most preferred herein is methylcellulose.

The polyethylene glycol useful for gelling is typically a mixture of low and high molecular weight polyethylene glycols to obtain the proper viscosity. For example, a mixture of a polyethylene glycol of molecular weight 400–600 with one of molecular weight 1500 would be effective for this purpose when mixed in the proper ratio to obtain a paste.

The term "water soluble" as applied to the polysaccharides and polyethylene glycols is meant to include colloidal solutions and dispersions. In general, the solubility of the cellulose derivatives is determined by the degree of substitution of ether groups, and the stabilizing derivatives useful herein should have a sufficient quantity of such ether groups per anhydroglucose unit in the cellulose chain to render the derivatives water soluble. A degree of ether substitution of at least 0.35 ether groups per anhydroglucose unit is generally sufficient. Additionally, the cellulose derivatives may be in the form of alkali metal salts, for example, the Li, Na, K, or Cs salts.

In a preferred embodiment, the gel contains about 2–5% by weight methylcellulose and the TGF-$\beta$ is present in an amount of about 10–1000 $\mu$g per ml of gel. More preferably, the gel consists of about 3% methylcellulose by weight, lactic acid to pH 5.0, and 20–200 $\mu$g per ml of TGF-$\beta$. This corresponds to a dose of 1–10 $\mu$g of TGF-$\beta$ per 50 $\mu$l of gel.

For the preparation of a sustained-release formulation, the TGF-$\beta$ is suitably incorporated into a biodegradable matrix or microcapsular particle. A suitable material for this purpose is a polylactide, although other polymers of poly ($\alpha$-hydroxycarboxylic acids), such as poly-D-(−)-3-hydroxybutyric acid (EP 133,988A), can be used. Additional biodegradable polymers include poly(lactones), poly(acetals), poly(orthoesters) or poly(orthocarbonates). The TGF-$\beta$ is also suitably mixed with a biodegradable protein carrier such as collagen, atelocollagen, or gelatin to form a carrier matrix having sustained-release properties; the resultant mixture is then dried, and the dried material is formed into an appropriate shape, as described in U.S. Pat. No. 4,774,091.

The initial consideration here must be that the carrier itself, or its degradation products, are non-toxic in the target bone site and will not further aggravate the condition. This can be determined by routine screening in animal models of the target bone disorder or, if such models are unavailable, in normal animals. For examples of sustained-release compositions, see U.S. Pat. No. 3,773,919, EP 58,481A, U.S. Pat. No. 3,887,699, EP 158,277A, Canadian Patent No. 1176565, U. Sidman et el., *Biopolymers*, 22:547 (1983), and R. Langer et al., *Chem. Tech.*, 12:98 (1982).

Controlled delivery of TGF-$\beta$ to a site also is suitably accomplished using permeable hollow cellulose acetate fibers with the TGF-$\beta$ and placed in the site and removed 24 hours later or left for longer periods of time (U.S. Pat. No. 4,175,326). Also, acrylic resin strips or cast films can be impregnated with TGF-$\beta$ and applied to the affected site. In addition, narrow dialysis tubing can be filled with a TGF-$\beta$ solution and placed so as to deliver TGF-$\beta$ to the appropriate site.

The composition herein also may suitably contain other peptide growth factors such as IGF-I, TGF-$\alpha$, human growth hormone, epidermal growth factor, and PDGF, provided that such factors do not include the bone morphogenetic factors defined above. Such growth factors are suitably present in an amount that is effective for the purpose intended, i.e., to promote formation of bone.

The invention will be more fully understood by reference to the following examples. They should not, however, be construed as limiting the scope of the invention. All literature citations are incorporated by reference.

EXAMPLE 1

The TGF-$\beta$1 used herein was the recombinant expression product of transfected human 293 cells as described by EP 260,341, supra, and by Derynck et el., *Nature*, 316: 701–705 (1985). The individual samples of recombinant human TGF-$\beta$1 (rHTGF-$\beta$1) were sterilely prepared in methylcellulose containing 20 mM sodium acetate buffer at pH 5.0 and applied as a single topical dose. Selected concentrations of rhTGF-$\beta$1 were mixed with methylcellulose gel so that the final concentration of methylcellulose was 3%. The vehicle was formulated in a similar manner without rhTGF-$\beta$1 as a control. The material was stored at 5° C. until use.

The rat incisional model utilized young adult Simonsen Albino rats (300–350 g). Full thickness skin incisions were made by cutting through the subdermal panniculus carnosus musculature following Betadine and 70% alcohol scrubbing to sterilize the wound. Two pairs of symmetrical transverse incisions (approximately 2.5 cm) were placed in each animal. A single dose of rhTGF-$\beta$1 in methylcellulose was placed into each stainless steel sutured wound by inserting a 25-gauge needle along the edge of the wound and below the sutures. The volume of rhTGF-$\beta$1 in 3% methylcellulose placed into each wound was 0.05 ml. Each rat had two incisions into which rhTGF-$\beta$1 in 3% methylcellulose was applied. One incision received either vehicle alone (3% methylcellulose) or no treatment at all. Concentrations of rhTGF-$\beta$1 were 500, 1000, 2000, or 4000 ng/ml. Dose-response curves were developed using dose ranges of 5 to 10,000 ng/wound. Animals were euthanized on day 5, 7, 10, 14, 21, and 28. The entire dorsal skin was excised after the sutures were removed. Two 8-mm wide strips of skin were collected from each incision and fixed in 10% neutral buffered formalin for seven days.

New Zealand white male rabbits (2.5–2.8 kg) were purchased from Elkhorn rabbitry. Anesthesia was induced by an intramuscular injection of ketamine hydrochloride/xylazine hydrochloride mixture. After removal of hair from the ears, the area of the wound was sterilely prepared using Betadine with an alcohol rinse. A circular 6-mm punch biopsy instrument was used to produce wounds to the depth of the ear cartilage. The underlying perichondrium was removed with a periosteal elevator and fine scissors. Wounds were treated with 0.025 ml of 3% methylcellulose or 5, 15, 25, 100, 500, or 1000 ng of rhTGF-$\beta$1 in 3% methylcellulose (control). Opsite TM surgical dressing was placed over each wound. An Elizabethian collar was placed around the neck of the rabbits to prevent mechanical disruption of the wounds by the rabbit.

Studies were also designed to examine short-term and long-term effects of topical rhTGF-$\beta$1. Wounds were harvested on days 3, 5, 7, 14, 21, 28, 42, 56, and 70. Wounds were photographed, cut into hemisections, and fixed in 10% neutral buffered formalin for histology and morphometric analysis. Morphometric analysis included measurements of total healing wound area, closing wound area, upper wound gap, lower wound gap, area of collagen, area of granulation tissue, epithelial cell layer length, and bone formation. These measurements were made on the Bioquant System IV analyzer.

Figure 2:
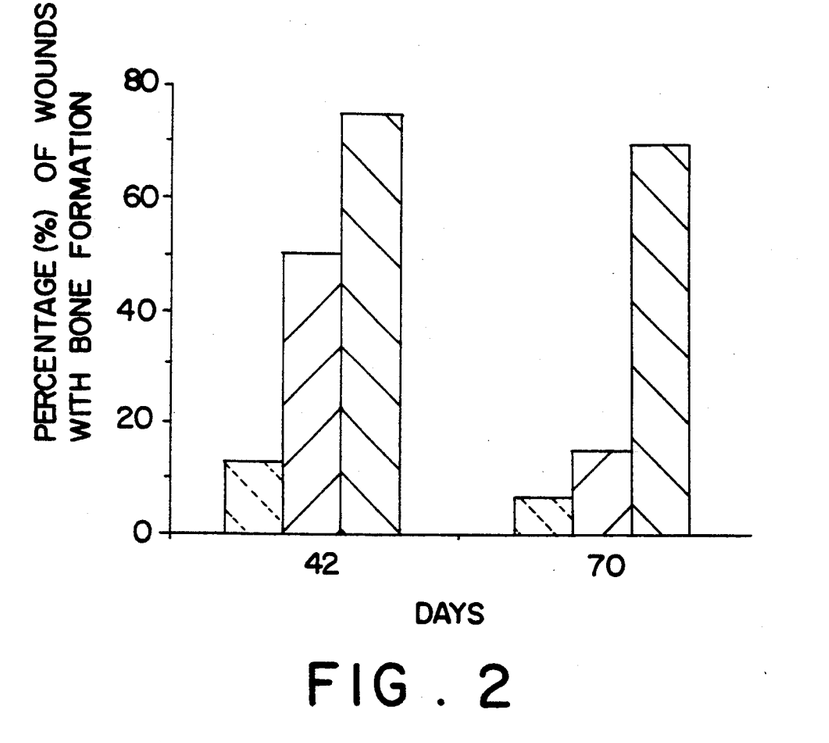
FIG. 2 illustrates the percentage of wounds with bone formation when placebo (left-most bar), recombinant human TGF-1 (rhTGF-$\beta$1) at 25 ng/wound (middle bar), or rhTGF-$\beta$1 at 100 ng/wound (right-most bar) is applied in the rabbit ear ulcer model at 42 and 70 days after wounding. Maximum bone formation was observed at day 42.

The rabbit ear ulcers were examined for delayed effects of rhTGF-$\beta$1 on days 21, 28, 42, 56, and 70 following a single application of 25 or 100 ng/wound on the day of wounding. Bone formation was observed along the wound edges and immediately adjacent to the cartilage. The bone was normal in morphological appearance, consisting of endochondral or membranous type bone and ossification with marrow spaces. Osteoblasts and osteoclasts were present. The percentage of wounds with bone increased to a maximum of 74% of the treated wounds at day 42 (100 ng/wound) and decreased to 69% by day 70. See FIG. 2. Bone formation was observed in less than 12% of placebo-treated wounds.

No bone formation was observed in the rat incision model, indicating that bone formation is induced only at a site that has a source of precursor (osteogenic) cells, in this case in the rabbit ear model where the wound was adjacent to perichondrium.

EXAMPLE 2

A rat femur gap model was employed wherein a polyethylene plate 2 mm thick, 8–10 mm long, and 4–5 mm wide was pinned to one face of a rat femur with stainless steel pins. From the center of the femur a 5–8 mm long piece of bone was removed. The plate serves to keep the gap in bone separated. This model is intended to mimic a nonunion fracture in a human.

Set into the gap in the femur is a porous cylindrical 200–400 micron ceramic implant of 60% by weight hydroxyapatite and 40% by weight tricalcium phosphate (Zimmer, Inc.), which is either (1) implant alone, (2) implant presoaked for 1 hour in a solution of 50 ng/ml TGF-$\beta$1 prepared as described in Example 1 and formulated in Delbecco's medium without serum, (3) implant plus dispersed whole bone marrow cells obtained from syngeneic rat, and (4) implant plus dispersed whole bone marrow cells pretreated with 50 ng/ml of the TGF-$\beta$1 in Delbecco's medium described above. A total of 15 rats were used for each of these four groups. One month after implant, the rats were sacrificed and analyzed for histological changes.

Preliminary results indicate that no bone replacement was observed in the control without cells or TGF-$\beta$ nor with TGF-$\beta$ without cells; TGF-$\beta$ with cells was found to accelerate the rate of bone growth over cells alone. The bone formed with TGF-$\beta$ was found in the interstices of the pores in the ceramic and bridged the gap. The bone formed with the TGF-$\beta$ was found to be histologically normal.

EXAMPLE 3

A case study was performed using baboons to investigate the effect of TGF-$\beta$ on bone wound healing. The baboon was selected because of the close analogy of its bone kinetics to those of man. A methylcellulose gel of TGF-$\beta$1 was delivered via an analytical bone implant, and after 22 days the implant was removed from the baboon. Tissue obtained from TGF-$\beta$ implant sites was analyzed using quantitative histomorphometry to determine the mean effect of TGF-$\beta$ on bone wound healing. Detailed non-quantitative histopathologic evaluation was also performed.

More specifically, four male baboons were implanted with four titanium analytical bone implants (cages) each, two per tibia in areas of close structural geometry. Holes were drilled in the tibia to allow implantation. After implantation, the baboons were allowed to heal for 41 days. On the 41st day, all the implant sites were surgically exposed, tissue was removed, and the test materials were implanted into the implant cores. Each animal received a normal (no treatment) control, a control with only methylcellulose vehicle, and a low (1 $\mu$g rhTGF-$\beta$ in methylcellulose) or high (10 $\mu$g rhTGF-$\beta$ in methylcellulose) dosage of active TGF-$\beta$. Specifically, these formulations each consisted of 1 g of 3.0% methylcellulose by weight, lactic acid QS to pH 5.0, and 0, 20, or 200 $\mu$g/ml of rhTGF-$\beta$1 prepared as described in Example 1. The formulations were poured into size 5 gelatin capsules (Elanco), which were then placed in the core of the titanium implant and used to deliver 50 $\mu$l of each formulation, with slow dissolution of the capsule. All implant sites within an animal were randomly assigned to one of the four treatments.

Following 22 days of healing, tissue in ali implants was retrieved. The tissue samples were placed in 10% formalin solution, buffered to a pH of 7.0, containing formaldehyde at 3.7% for fixation. Samples were submitted for histopathologic analysis.

The following descriptive and quantitative observations were made:

1. Bone volume in TGF-$\beta$ sites was lower than control and placebo sites, although not statistically significant.
2. Osteoblast numbers, volume, and activity were significantly greater in the TGF-$\beta$ sites when compared to either the control or placebo.
3. Osteoclast numbers and activity appeared higher in all four treatment sites when subjectively compared to control data obtained in previous studies.
4. Residual methylcellulose was noted and appeared to require phagocytosis before new trabecular bone could form.
5. TGF-$\beta$ in the presence of methylcellulose matrix was associated with increased numbers of fibroblast, osteoprogenitor cells, and osteoblasts.

6. No foreign body response or other adverse pathologic reaction to either matrix alone or matrix and TGF-β was observed.

7. Significant periosteal new bone formation was noted over the implants in five TGF-β sites in three animals. Bone formation over the implant to this degree had never been observed in over 450 titanium implant procedures carried out over the past few years.

8. TGF-β sites were identified during blinded histologic review in seven out of a total of eight sites.

9. Methylcellulose sites were identified during blinded histologic review 100% of the time.

Control samples analyzed in this study demonstrated that cancellous tissue formed in the titanium implant is stratified from inferior to superior aspects of the implant core. The superior portion of the tissue (closest to the cap of the titanium implant) is less mature and shows treater osteoblastic activity, while tissue near the inferior aspects of the implant and deep within the medullary compartment is more mature in morphology and shows a reduced osteoblastic population and activity. In contrast to historical and control samples, the TGF-β tissue samples were homogeneous in their high osteoblastic activity throughout the specimen.

Clinical observations of the tissue above and around the supraperiosteal portion of the titanium implant revealed pronounced periosteal bone formation. This periosteal bone formed large masses over two sites in each of two animals. The masses in these two animals were highly vascularized, had the clinical appearance of trabecular bone, and varied in size within one animal. The two masses in each of two animals were approximately 3×2×1.5 cm and 1.5×1×0.5 cm in size. One additional animal demonstrated pronounced periosteal bone formation over one TGF-β site. It is significant that in over 430 titanium implant surgical procedures masses like these have never formed over the titanium implants. Histologically, this periosteal bone formation over five TGF-β sites in three baboons was similar to an actively healing, uncomplicated, fracture callus, i.e., morphologically normal, mature bone formation.

In general, the methylcellulose was well tolerated and no foreign body response was present in any of the four treatment sites. Additionally, no evidence of cytologic atypia or malignancy was found in either titanium implants or periosteal samples.

---

What is claimed is:

1. A pharmaceutical composition for treatment of a site of an animal where skeletal tissue is deficient consisting essentially of about 1 to 100 ng/ml of TGF-$\beta$ and an osteogenic cell source isolated from an animal, which composition is formulated in a pharmaceutically acceptable carrier and excludes a bone morphogenetic cofactor.

2. The composition of claim 1 wherein the osteogenic cell source is dispersed whole bone marrow, perichondrium, periosteum, or a cell line.

3. The composition of claim 1 wherein the TGF-$\beta$ is TGF-$\beta$1 or TGF-$\beta$3.

* * * * *

UNITED STATES PATENT AND TRADEMARK OFFICE
CERTIFICATE OF CORRECTION

PATENT NO. : 5,409,896
DATED : April 25, 1995
INVENTOR(S) : Ammann and Rudman

Figure 1A:
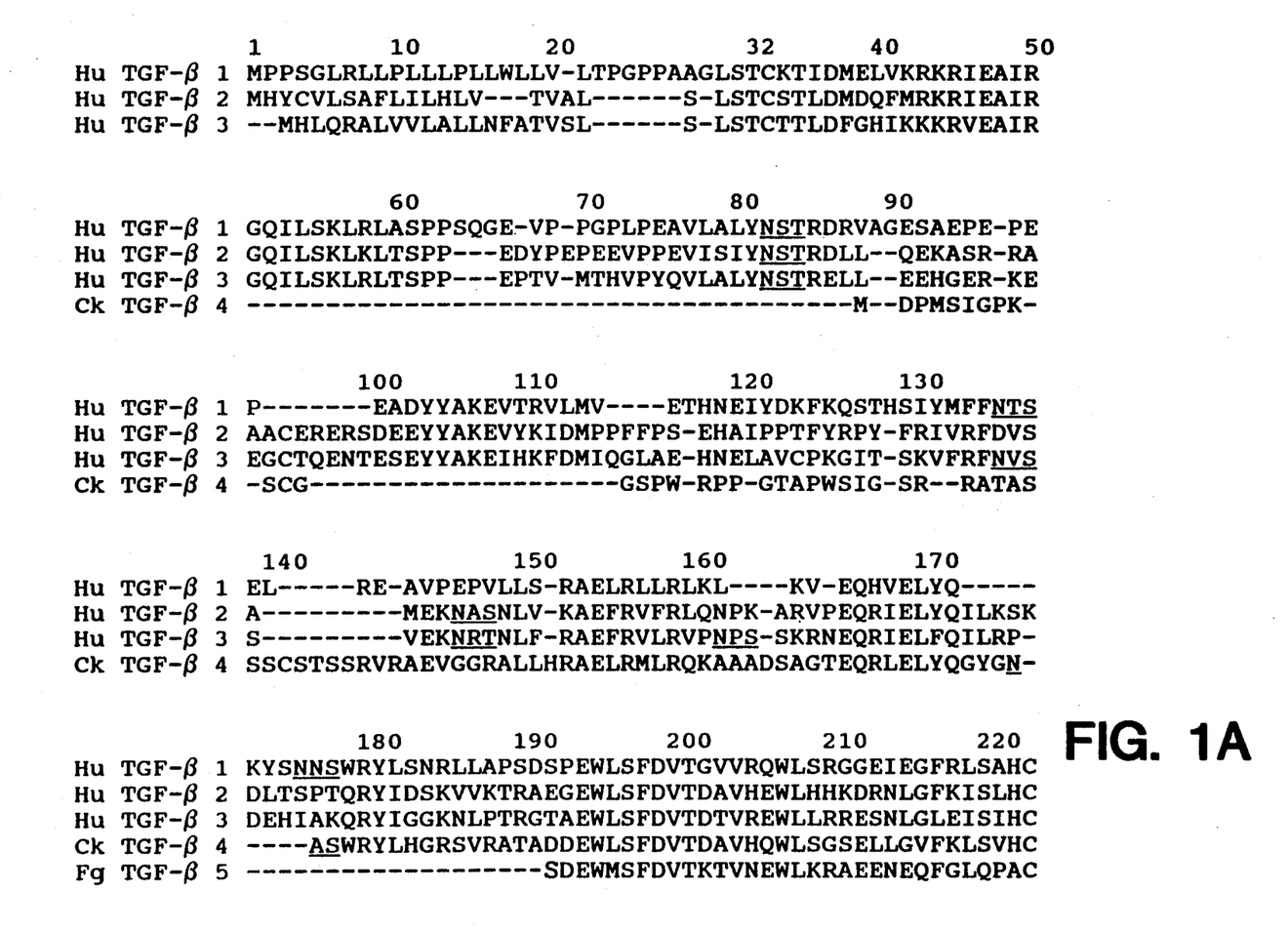
FIGS. 1A and 1B illustrate the sequences of human TGF-$\beta$1 (SEQ. ID. No. 1), human TGF-$\beta$2 (SEQ. ID. No. 2), human TGF-$\beta$3 (SEQ. ID. No. 3), chick TGF-$\beta$4 (SEQ. ID. No. 4), and frog TGF-$\beta$5 (SEQ. ID. No. 5).
Figure 1B:
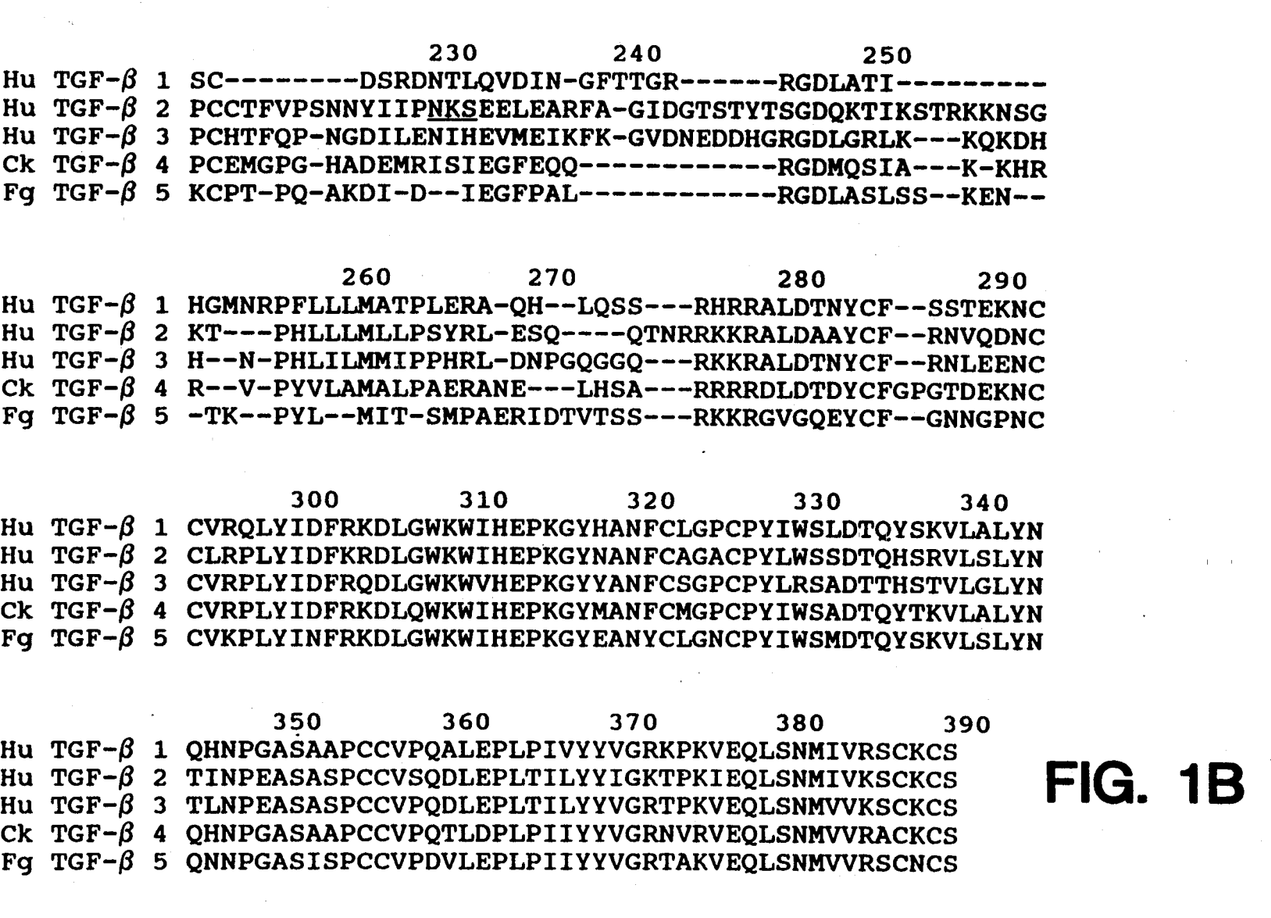

It is certified that error appears in the above-indentified patent and that said Letters Patent is hereby corrected as shown below:

IN THE DRAWINGS:

In Figure 1A, line 3, please delete "Hu TGF-$\beta$ 3 --" and replace it as follows: --Hu TGF-$\beta$ 3 MK--".

Signed and Sealed this

Thirtieth Day of January, 1996

Attest:

BRUCE LEHMAN

*Attesting Officer*   *Commissioner of Patents and Trademarks*

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 390 amino acids
        ( B ) TYPE: amino acid
        ( D ) TOPOLOGY: linear     ( x i ) SEQUENCE DESCRIPTION: SEQ ID NO:1:

```
Met Pro Pro Ser Gly Leu Arg Leu Leu Pro Leu Leu Leu Pro Leu
 1           5                   10                      15

Leu Trp Leu Leu Val Leu Thr Pro Gly Pro Pro Ala Ala Gly Leu
            20                  25                      30

Ser Thr Cys Lys Thr Ile Asp Met Glu Leu Val Lys Arg Lys Arg
            35                  40                      45

Ile Glu Ala Ile Arg Gly Gln Ile Leu Ser Lys Leu Arg Leu Ala
            50                  55                      60

Ser Pro Pro Ser Gln Gly Glu Val Pro Pro Gly Pro Leu Pro Glu
            65                  70                      75

Ala Val Leu Ala Leu Tyr Asn Ser Thr Arg Asp Arg Val Ala Gly
            80                  85                      90

Glu Ser Ala Glu Pro Glu Pro Glu Pro Glu Ala Asp Tyr Tyr Ala
            95                  100                     105

Lys Glu Val Thr Arg Val Leu Met Val Glu Thr His Asn Glu Ile
            110                 115                     120

Tyr Asp Lys Phe Lys Gln Ser Thr His Ser Ile Tyr Met Phe Phe
            125                 130                     135

Asn Thr Ser Glu Leu Arg Glu Ala Val Pro Glu Pro Val Leu Leu
            140                 145                     150

Ser Arg Ala Glu Leu Arg Leu Leu Arg Leu Lys Leu Lys Val Glu
            155                 160                     165

Gln His Val Glu Leu Tyr Gln Lys Tyr Ser Asn Asn Ser Trp Arg
            170                 175                     180
```

```
Tyr Leu Ser Asn Arg Leu Leu Ala Pro Ser Asp Ser Pro Glu Trp
            185                 190                 195

Leu Ser Phe Asp Val Thr Gly Val Val Arg Gln Trp Leu Ser Arg
            200                 205                 210

Gly Gly Glu Ile Glu Gly Phe Arg Leu Ser Ala His Cys Ser Cys
            215                 220                 225

Asp Ser Arg Asp Asn Thr Leu Gln Val Asp Ile Asn Gly Phe Thr
            230                 235                 240

Thr Gly Arg Arg Gly Asp Leu Ala Thr Ile His Gly Met Asn Arg
            245                 250                 255

Pro Phe Leu Leu Leu Met Ala Thr Pro Leu Glu Arg Ala Gln His
            260                 265                 270

Leu Gln Ser Ser Arg His Arg Arg Ala Leu Asp Thr Asn Tyr Cys
            275                 280                 285

Phe Ser Ser Thr Glu Lys Asn Cys Cys Val Arg Gln Leu Tyr Ile
            290                 295                 300

Asp Phe Arg Lys Asp Leu Gly Trp Lys Trp Ile His Glu Pro Lys
            305                 310                 315

Gly Tyr His Ala Asn Phe Cys Leu Gly Pro Cys Pro Tyr Ile Trp
            320                 325                 330

Ser Leu Asp Thr Gln Tyr Ser Lys Val Leu Ala Leu Tyr Asn Gln
            335                 340                 345

His Asn Pro Gly Ala Ser Ala Ala Pro Cys Cys Val Pro Gln Ala
            350                 355                 360

Leu Glu Pro Leu Pro Ile Val Tyr Tyr Val Gly Arg Lys Pro Lys
            365                 370                 375

Val Glu Gln Leu Ser Asn Met Ile Val Arg Ser Cys Lys Cys Ser
            380                 385                 390
```

( 2 ) INFORMATION FOR SEQ ID NO:2:

( i ) SEQUENCE CHARACTERISTICS:
        ( A ) LENGTH: 414 amino acids
        ( B ) TYPE: amino acid
        ( D ) TOPOLOGY: linear     ( x i ) SEQUENCE DESCRIPTION: SEQ ID NO:2:

```
Met His Tyr Cys Val Leu Ser Ala Phe Leu Ile Leu His Leu Val
 1               5                  10                  15

Thr Val Ala Leu Ser Leu Ser Thr Cys Ser Thr Leu Asp Met Asp
            20                  25                  30

Gln Phe Met Arg Lys Arg Ile Glu Ala Ile Arg Gly Gln Ile Leu
            35                  40                  45

Ser Lys Leu Lys Leu Thr Ser Pro Pro Glu Asp Tyr Pro Glu Pro
            50                  55                  60

Glu Glu Val Pro Pro Glu Val Ile Ser Ile Tyr Asn Ser Thr Arg
            65                  70                  75

Asp Leu Leu Gln Glu Lys Ala Ser Arg Arg Ala Ala Ala Cys Glu
            80                  85                  90

Arg Glu Arg Ser Asp Glu Glu Tyr Tyr Ala Lys Glu Val Tyr Lys
            95                  100                 105

Ile Asp Met Pro Pro Phe Phe Pro Ser Glu Asn Ala Ile Pro Pro
            110                 115                 120

Thr Phe Tyr Arg Pro Tyr Phe Arg Ile Val Arg Phe Asp Val Ser
            125                 130                 135

Ala Met Glu Lys Asn Ala Ser Asn Leu Val Lys Ala Glu Phe Arg
            140                 145                 150
```

| | | | | | | | | | | | | | |
|---|---|---|---|---|---|---|---|---|---|---|---|---|---|
|Val|Phe|Arg|Leu|Gln<br>155|Asn|Pro|Lys|Ala|Arg<br>160|Val|Pro|Glu|Gln|Arg<br>165|
|Ile|Glu|Leu|Tyr|Gln<br>170|Ile|Leu|Lys|Ser|Lys<br>175|Asp|Leu|Thr|Ser|Pro<br>180|
|Thr|Gln|Arg|Tyr|Ile<br>185|Asp|Ser|Lys|Val|Val<br>190|Lys|Thr|Arg|Ala|Glu<br>195|
|Gly|Glu|Trp|Leu|Ser<br>200|Phe|Asp|Val|Thr|Asp<br>205|Ala|Val|His|Glu|Trp<br>210|
|Leu|His|His|Lys|Asp<br>215|Arg|Asn|Leu|Gly|Phe<br>220|Lys|Ile|Ser|Leu|His<br>225|
|Cys|Pro|Cys|Cys|Thr<br>230|Phe|Val|Pro|Ser|Asn<br>235|Asn|Tyr|Ile|Ile|Pro<br>240|
|Asn|Lys|Ser|Glu|Glu<br>245|Leu|Glu|Ala|Arg|Phe<br>250|Ala|Gly|Ile|Asp|Gly<br>255|
|Thr|Ser|Thr|Tyr|Thr<br>260|Ser|Gly|Asp|Gln|Lys<br>265|Thr|Ile|Lys|Ser|Thr<br>270|
|Arg|Lys|Lys|Asn|Ser<br>275|Gly|Lys|Thr|Pro|His<br>280|Leu|Leu|Leu|Met|Leu<br>285|
|Leu|Pro|Ser|Tyr|Arg<br>290|Leu|Glu|Ser|Gln|Gln<br>295|Thr|Asn|Arg|Arg|Lys<br>300|
|Lys|Arg|Ala|Leu|Asp<br>305|Ala|Ala|Tyr|Cys|Phe<br>310|Arg|Asn|Val|Gln|Asp<br>315|
|Asn|Cys|Cys|Leu|Arg<br>320|Pro|Leu|Tyr|Ile|Asp<br>325|Phe|Lys|Arg|Asp|Leu<br>330|
|Gly|Trp|Lys|Trp|Ile<br>335|His|Glu|Pro|Lys|Gly<br>340|Tyr|Asn|Ala|Asn|Phe<br>345|
|Cys|Ala|Gly|Ala|Cys<br>350|Pro|Tyr|Leu|Trp|Ser<br>355|Ser|Asp|Thr|Gln|His<br>360|
|Ser|Arg|Val|Leu|Ser<br>365|Leu|Tyr|Asn|Thr|Ile<br>370|Asn|Pro|Glu|Ala|Ser<br>375|
|Ala|Ser|Pro|Cys|Cys<br>380|Val|Ser|Gln|Asp|Leu<br>385|Glu|Pro|Leu|Thr|Ile<br>390|
|Leu|Tyr|Tyr|Ile|Gly<br>395|Lys|Thr|Pro|Lys|Ile<br>400|Glu|Gln|Leu|Ser|Asn<br>405|
|Met|Ile|Val|Lys|Ser<br>410|Cys|Lys|Cys|Ser<br>414| | | | | |

(2) INFORMATION FOR SEQ ID NO:3:

( i ) SEQUENCE CHARACTERISTICS:
        ( A ) LENGTH: 412 amino acids
        ( B ) TYPE: amino acid
        ( D ) TOPOLOGY: linear     ( x i ) SEQUENCE DESCRIPTION: SEQ ID NO:3:

| | | | | | | | | | | | | | | |
|---|---|---|---|---|---|---|---|---|---|---|---|---|---|---|
|Met<br>1|Lys|Met|His|Leu<br>5|Gln|Arg|Ala|Leu|Val<br>10|Val|Leu|Ala|Leu|Leu<br>15|
|Asn|Phe|Ala|Thr|Val<br>20|Ser|Leu|Ser|Leu|Ser<br>25|Thr|Cys|Thr|Thr|Leu<br>30|
|Asp|Phe|Gly|His|Ile<br>35|Lys|Lys|Lys|Arg|Val<br>40|Glu|Ala|Ile|Arg|Gly<br>45|
|Gln|Ile|Leu|Ser|Lys<br>50|Leu|Arg|Leu|Thr|Ser<br>55|Pro|Pro|Glu|Pro|Thr<br>60|
|Val|Met|Thr|His|Val<br>65|Pro|Tyr|Gln|Val|Leu<br>70|Ala|Leu|Tyr|Asn|Ser<br>75|
|Thr|Arg|Glu|Leu|Leu<br>80|Glu|Glu|His|Gly|Glu<br>85|Arg|Lys|Glu|Glu|Gly<br>90|

Cys Thr Gln Glu Asn Thr Glu Ser Glu Tyr Tyr Ala Lys Glu Ile
                95                    100                   105

His Lys Phe Asp Met Ile Gln Gly Leu Ala Glu His Asn Glu Leu
                110                   115                   120

Ala Val Cys Pro Lys Gly Ile Thr Ser Lys Val Phe Arg Phe Asn
                125                   130                   135

Val Ser Ser Val Glu Lys Asn Arg Thr Asn Leu Phe Arg Ala Glu
                140                   145                   150

Phe Arg Val Leu Arg Val Pro Asn Pro Ser Ser Lys Arg Asn Glu
                155                   160                   165

Gln Arg Ile Glu Leu Phe Gln Ile Leu Arg Pro Asp Glu His Ile
                170                   175                   180

Ala Lys Gln Arg Tyr Ile Gly Gly Lys Asn Leu Pro Thr Arg Gly
                185                   190                   195

Thr Ala Glu Trp Leu Ser Phe Asp Val Thr Asp Thr Val Arg Glu
                200                   205                   210

Trp Leu Leu Arg Arg Glu Ser Asn Leu Gly Leu Glu Ile Ser Ile
                215                   220                   225

His Cys Pro Cys His Thr Phe Gln Pro Asn Gly Asp Ile Leu Glu
                230                   235                   240

Asn Ile His Glu Val Met Glu Ile Lys Phe Lys Gly Val Asp Asn
                245                   250                   255

Glu Asp Asp His Gly Arg Gly Asp Leu Gly Arg Leu Lys Lys Gln
                260                   265                   270

Lys Asp Asn Asn Asn Pro His Leu Ile Leu Met Met Ile Pro Pro
                275                   280                   285

His Arg Leu Asp Asn Pro Gly Gln Gly Gly Gln Arg Lys Lys Arg
                290                   295                   300

Ala Leu Asp Thr Asn Tyr Cys Phe Arg Asn Leu Glu Glu Asn Cys
                305                   310                   315

Cys Val Arg Pro Leu Tyr Ile Asp Phe Arg Gln Asp Leu Gly Trp
                320                   325                   330

Lys Trp Val His Glu Pro Lys Gly Tyr Tyr Ala Asn Phe Cys Ser
                335                   340                   345

Gly Pro Cys Pro Tyr Leu Arg Ser Ala Asp Thr Thr His Ser Thr
                350                   355                   360

Val Leu Gly Leu Tyr Asn Thr Leu Asn Pro Glu Ala Ser Ala Ser
                365                   370                   375

Pro Cys Cys Val Pro Gln Asp Leu Glu Pro Leu Thr Ile Leu Tyr
                380                   385                   390

Tyr Val Gly Arg Thr Pro Lys Val Glu Gln Leu Ser Asn Met Val
                395                   400                   405

Val Lys Ser Cys Lys Cys Ser
                410       412

( 2 ) INFORMATION FOR SEQ ID NO:4:

( i ) SEQUENCE CHARACTERISTICS:
        ( A ) LENGTH: 304 amino acids
        ( B ) TYPE: amino acid
        ( D ) TOPOLOGY: linear     ( x i ) SEQUENCE DESCRIPTION: SEQ ID NO:4:

Met Asp Pro Met Ser Ile Gly Pro Lys Ser Cys Gly Gly Ser Pro
 1              5                     10                    15

Trp Arg Pro Pro Gly Thr Ala Pro Trp Ser Ile Gly Ser Arg Arg
                20                    25                    30

```
Ala  Thr  Ala  Ser  Ser  Ser  Cys  Ser  Thr  Ser  Ser  Arg  Val  Arg  Ala
               35                  40                  45

Glu  Val  Gly  Gly  Arg  Ala  Leu  Leu  His  Arg  Ala  Glu  Leu  Arg  Met
               50                  55                  60

Leu  Arg  Gln  Lys  Ala  Ala  Ala  Asp  Ser  Ala  Gly  Thr  Glu  Gln  Arg
               65                  70                  75

Leu  Glu  Leu  Tyr  Gln  Gly  Tyr  Gly  Asn  Ala  Ser  Trp  Arg  Tyr  Leu
               80                  85                  90

His  Gly  Arg  Ser  Val  Arg  Ala  Thr  Ala  Asp  Asp  Glu  Trp  Leu  Ser
               95                 100                 105

Phe  Asp  Val  Thr  Asp  Ala  Val  His  Gln  Trp  Leu  Ser  Gly  Ser  Glu
              110                 115                 120

Leu  Leu  Gly  Val  Phe  Lys  Leu  Ser  Val  His  Cys  Pro  Cys  Glu  Met
              125                 130                 135

Gly  Pro  Gly  His  Ala  Asp  Glu  Met  Arg  Ile  Ser  Ile  Glu  Gly  Phe
              140                 145                 150

Glu  Gln  Gln  Arg  Gly  Asp  Met  Gln  Ser  Ile  Ala  Lys  Lys  His  Arg
              155                 160                 165

Arg  Val  Pro  Tyr  Val  Leu  Ala  Met  Ala  Leu  Pro  Ala  Glu  Arg  Ala
              170                 175                 180

Asn  Glu  Leu  His  Ser  Ala  Arg  Arg  Arg  Arg  Asp  Leu  Asp  Thr  Asp
              185                 190                 195

Tyr  Cys  Phe  Gly  Pro  Gly  Thr  Asp  Glu  Lys  Asn  Cys  Cys  Val  Arg
              200                 205                 210

Pro  Leu  Tyr  Ile  Asp  Phe  Arg  Lys  Asp  Leu  Gln  Trp  Lys  Trp  Ile
              215                 220                 225

His  Glu  Pro  Lys  Gly  Tyr  Met  Ala  Asn  Phe  Cys  Met  Gly  Pro  Cys
              230                 235                 240

Pro  Tyr  Ile  Trp  Ser  Ala  Asp  Thr  Gln  Tyr  Thr  Lys  Val  Leu  Ala
              245                 250                 255

Leu  Tyr  Asn  Gln  His  Asn  Pro  Gly  Ala  Ser  Ala  Ala  Pro  Cys  Cys
              260                 265                 270

Val  Pro  Gln  Thr  Leu  Asp  Pro  Leu  Pro  Ile  Ile  Tyr  Tyr  Val  Gly
              275                 280                 285

Arg  Asn  Val  Arg  Val  Glu  Gln  Leu  Ser  Asn  Met  Val  Val  Arg  Ala
              290                 295                 300

Cys  Lys  Cys  Ser
              304
```

( 2 ) INFORMATION FOR SEQ ID NO:5:

( i ) SEQUENCE CHARACTERISTICS:
    ( A ) LENGTH: 199 amino acids
    ( B ) TYPE: amino acid
    ( D ) TOPOLOGY: linear   ( x i ) SEQUENCE DESCRIPTION: SEQ ID NO:5:

```
Ser  Asp  Glu  Trp  Met  Ser  Phe  Asp  Val  Thr  Lys  Thr  Val  Asn  Glu
 1                 5                  10                  15

Trp  Leu  Lys  Arg  Ala  Glu  Glu  Asn  Glu  Gln  Phe  Gly  Leu  Gln  Pro
               20                  25                  30

Ala  Cys  Lys  Cys  Pro  Thr  Pro  Gln  Ala  Lys  Asp  Ile  Asp  Ile  Glu
               35                  40                  45

Gly  Phe  Pro  Ala  Leu  Arg  Gly  Asp  Leu  Ala  Ser  Leu  Ser  Ser  Lys
               50                  55                  60

Glu  Asn  Thr  Lys  Pro  Tyr  Leu  Met  Ile  Thr  Ser  Met  Pro  Ala  Gly
               65                  70                  75
```

```
Arg Ile Asp Thr Val Thr Ser Ser Arg Lys Lys Arg Gly Val Gly
                80                    85              90
Gln Glu Tyr Cys Phe Gly Asn Asn Gly Pro Asn Cys Cys Val Lys
                95                   100             105
Pro Leu Tyr Ile Asn Phe Arg Lys Asp Leu Gly Trp Lys Trp Ile
               110                   115             120
His Glu Pro Lys Gly Tyr Glu Ala Asn Tyr Cys Leu Gly Asn Cys
               125                   130             135
Pro Tyr Ile Trp Ser Met Asp Thr Gln Tyr Ser Lys Val Leu Ser
               140                   145             150
Leu Tyr Asn Gln Asn Asn Pro Gly Ala Ser Ile Ser Pro Cys Cys
               155                   160             165
Val Pro Asp Val Leu Gly Pro Leu Pro Ile Ile Tyr Tyr Val Gly
               170                   175             180
Arg Thr Ala Lys Val Glu Gln Leu Ser Asn Met Val Val Arg Ser
               185                   190             195
Cys Asn Cys Ser
            199
```